United States Patent
Hanoun

(10) Patent No.: US 6,186,961 B1
(45) Date of Patent: Feb. 13, 2001

(54) PHYSICAL CAPACITY ASSESSMENT SYSTEM

(76) Inventor: Reed Hanoun, 50 Findlay Avenue, King City, Ontario (CA)

(*) Notice: Under 35 U.S.C. 154(b), the term of this patent shall be extended for 0 days.

(21) Appl. No.: 09/186,616

(22) Filed: Nov. 6, 1998

(51) Int. Cl.[7] ................................................. A61B 5/103
(52) U.S. Cl. ........................... 600/587; 73/379.01; 482/6; 482/9; 482/900
(58) Field of Search ..................................... 600/587, 594, 600/595; 73/379.01, 379.08, 379.09; 482/900, 3, 4, 6, 8, 9

(56) References Cited

U.S. PATENT DOCUMENTS 5,275,045 * 1/1994 Johnston ........................... 73/379.01
5,462,065 * 10/1995 Cusimano .......................... 600/587

* cited by examiner

Primary Examiner—John Mulcahy
Assistant Examiner—Victor K. Hwang

(57) ABSTRACT

A testing apparatus of a physical capacity assessment system has a support base, a column extending upwardly from the base and a workstation to which load is applied by an individual being tested on the apparatus. The workstation is supported by and adjustable in a number of different planes relative to the column. Also provided are an indicator which shows positioning of the workstation and a measuring device which measures the load placed on the workstation.

9 Claims, 11 Drawing Sheets

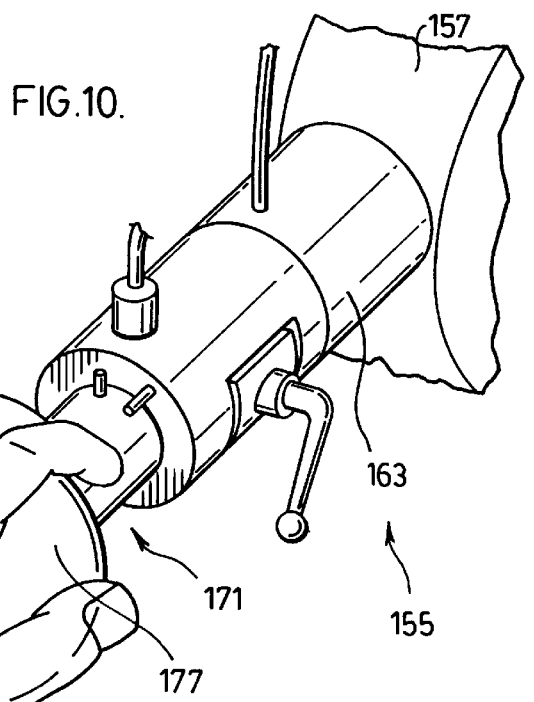
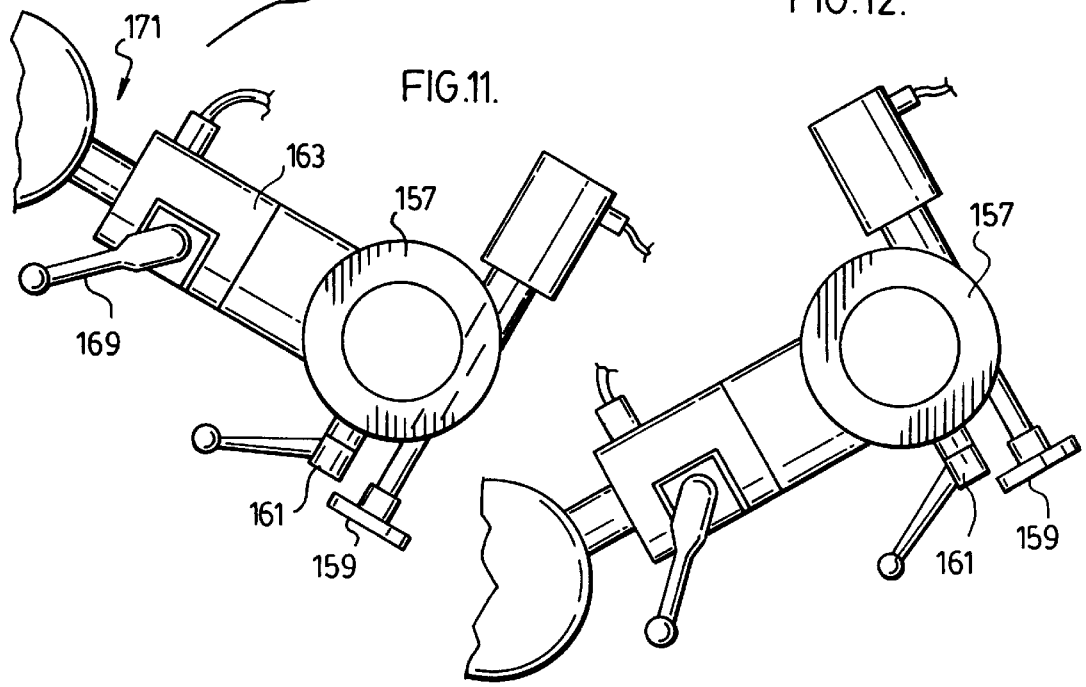
FIG. 10.
FIG. 11.
FIG. 12.

PHYSICAL CAPACITY ASSESSMENT SYSTEM

FIELD OF THE INVENTION

The present invention relates to a system for assessing an individual's physical capacity from both a strength and a range of motion standpoint.

BACKGROUND OF THE INVENTION

In today's society where on the job injuries occur in ever increasing numbers, it is extremely important to be able to assess an individual's physical capacity for both injury preventative and rehabilitation purposes.

By assessing an individual's physical strengths and weaknesses an employer can determine which jobs that individual should or should not perform. Furthermore, physical injuries, e.g. muscle strains and the like can be helped to heal by performing appropriate exercises. However, over exertion or working at the wrong exercises can be detrimental to such healing. These factors can only once again be determined by having an accurate assessment of the individual's physical capacities.

As a result of the growing number of people in the workforce, there are more and more claims against employers and ultimately insurance companies for on the job injuries. most of these claims are legitimate, but there are unfortunately also fraudulent claims. The legitimacy of a claim can be determined by means of a physical capacity assessment system.

In view of the above, there is a very real need for such as system.

SUMMARY OF THE INVENTION

The present invention relates to a physical capacity assessment system which is based on a testing apparatus at which physical tasks are performed by an individual being tested by the system. The apparatus has a support base, a column extending upwardly from the base and a workstation to which load is applied by the individual when performing the tasks. The workstation is supported by, and is adjustable in position in a number of different planes relative to, the column. The apparatus includes means which shows positioning of the workstation and means which measures load placed on the workstation.

According to the above features, the apparatus is usable by individuals of various different sizes and is further capable of having those individuals perform the tasks at various different positions on the apparatus.

According to an aspect of the present invention a method of assessing the physical capacity of an individual comprises putting the individual through a plurality of testing cycles in which each cycle consists of the individual moving a load of predetermined weight through a course of predetermined distance while monitoring both length of time and physical exertion on the individual to complete the course.

BRIEF DESCRIPTION OF THE DRAWINGS

The above as well as other advantages and features of the present invention will be described in greater detail according to the preferred embodiments of the present invention in which;

FIGS. 10 through 12 show various different uses and positionings of one of the hand tools from the workstation of FIG. 9;

DETAILED DESCRIPTION ACCORDING TO THE PREFERRED EMBODIMENTS OF THE PRESENT INVENTION

Figure 1:
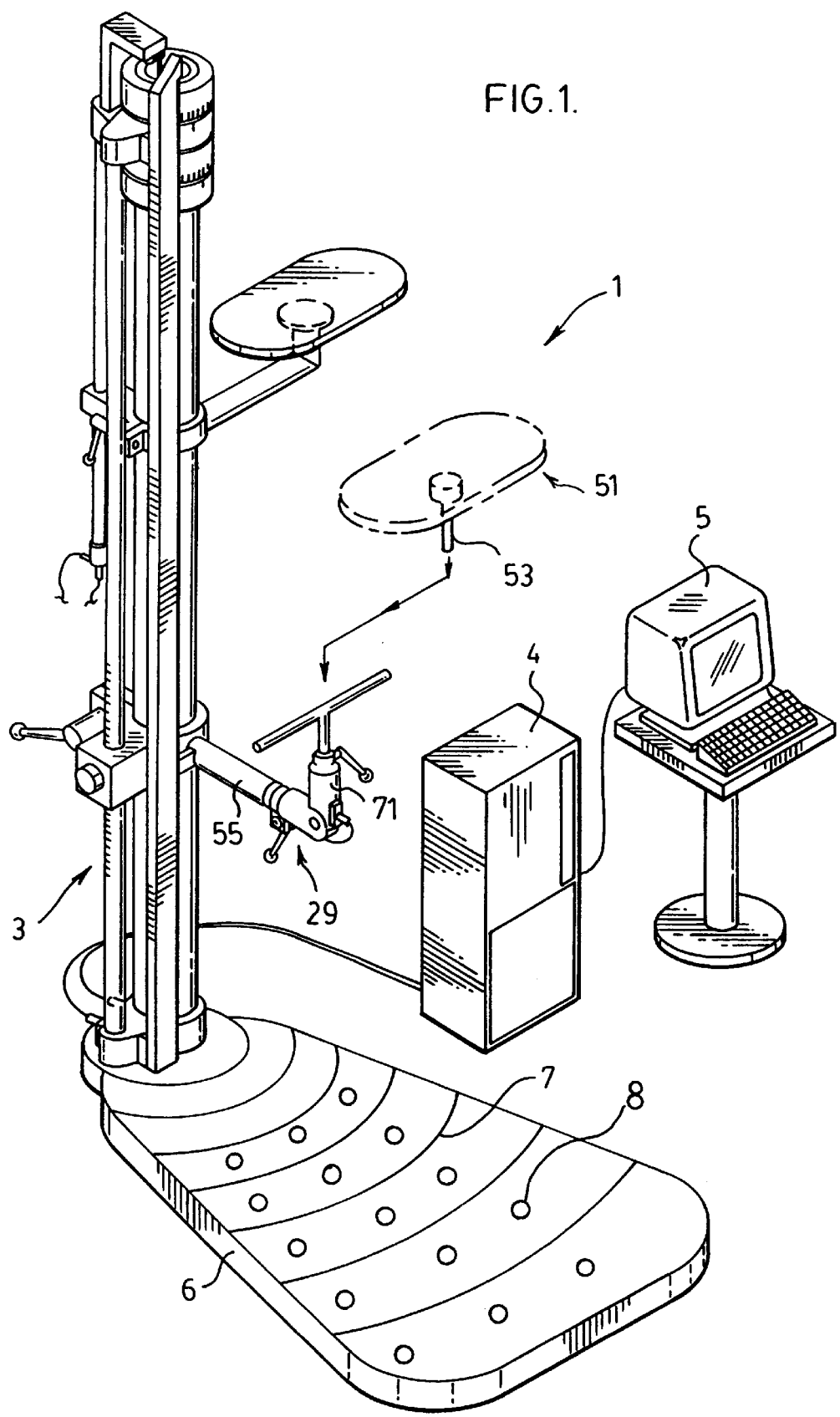
FIG. 1 is a perspective view of a physical capacity assessment system according to a preferred embodiment of the present invention.
Figure 7:
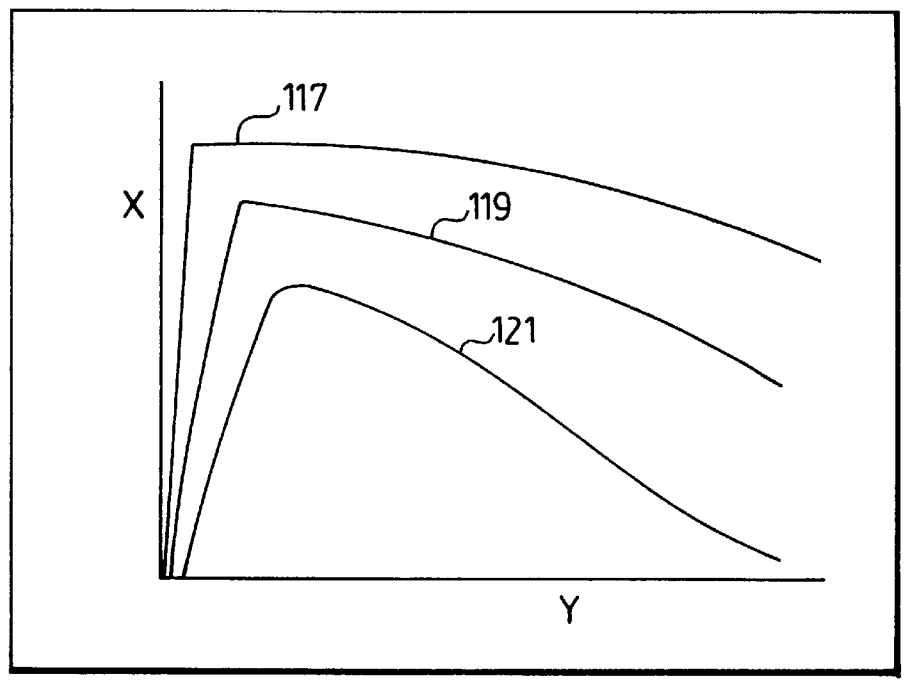
FIGS. 7 and 8 are graphs showing assessment of an individual using the system of FIG. 1.
Figure 8:
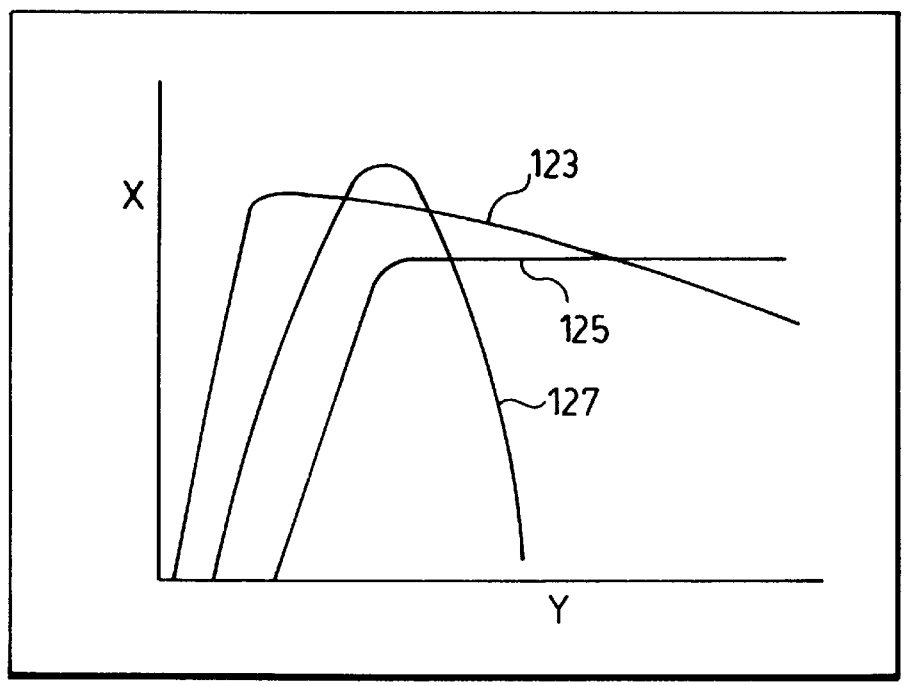

FIG. 1 shows a physical capacity assessment system generally indicated at 1. The heart of this system is based on a testing apparatus 3 which feeds information to a controller 4. This controller converts the information to visual images which are displayed on a monitor 5. Examples of these images are represented by the graphs of FIGS. 7 and 8 which will be described later in detail.

Testing apparatus 3 includes a base platform 6 on which an individual stands for performing some of the tests which can be carried out according to the present invention. Platform 6 includes markings 7 which provide accurate foot positioning of the individual. The platform also includes load sensors which sense weight of the individual to provide an electronic determination of foot positioning on the platform. This information is then fed to controller 4.

Figure 2:
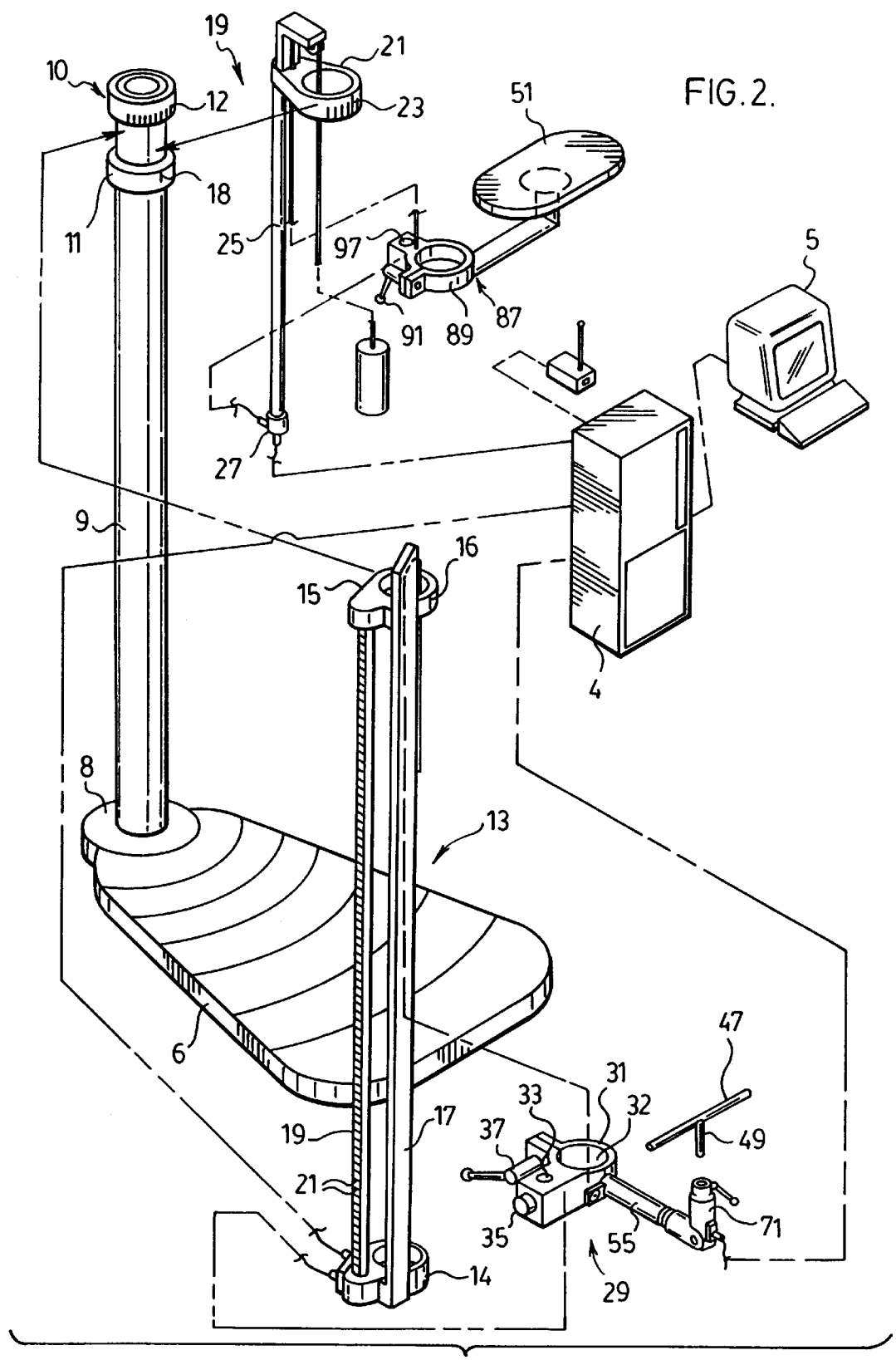
FIG. 2 is a view similar to FIG. 1 but showing the actual testing apparatus in exploded form.

As better seen in FIG. 2 of the drawings, a circular column 9 extends upwardly from the platform 6. This column supports at least one and in this case, two workstations. One of the workstations in FIG. 2 is generally indicated at 29. The other workstation is generally indicated at 87. Workstation 29 is located below and at a different orientation from workstation 87 relative to platform 6. This set up allows an individual to immediately move from one task to another. Some examples of different tasks will be described later in detail.

As per the description immediately below, the height of each of the workstations in the preferred embodiment is automatically determined in an extremely accurate manner by electronic sensors of the testing apparatus. This in its own is a very important feature because there are certain tasks which have to be performed at a specific height to provide proper test results. Testing apparatus 3 will not allow recording of these particular tasks unless the height requirement for the workstation is accurately set on the apparatus.

More particularly, the first workstation 29 couples and is used in conjunction with a first workstation guide 13. The second workstation 87 couples and works in conjunction with a second workstation guide 19.

Guide 13 comprises a lower collar 14 and an upper collar 15 which sleeve over column 9. The lower collar 14 seats atop the lower end 8 of the column. The upper collar 15 locates between two collars 10 and 11 provided on the column near its upper end.

Figure 3:
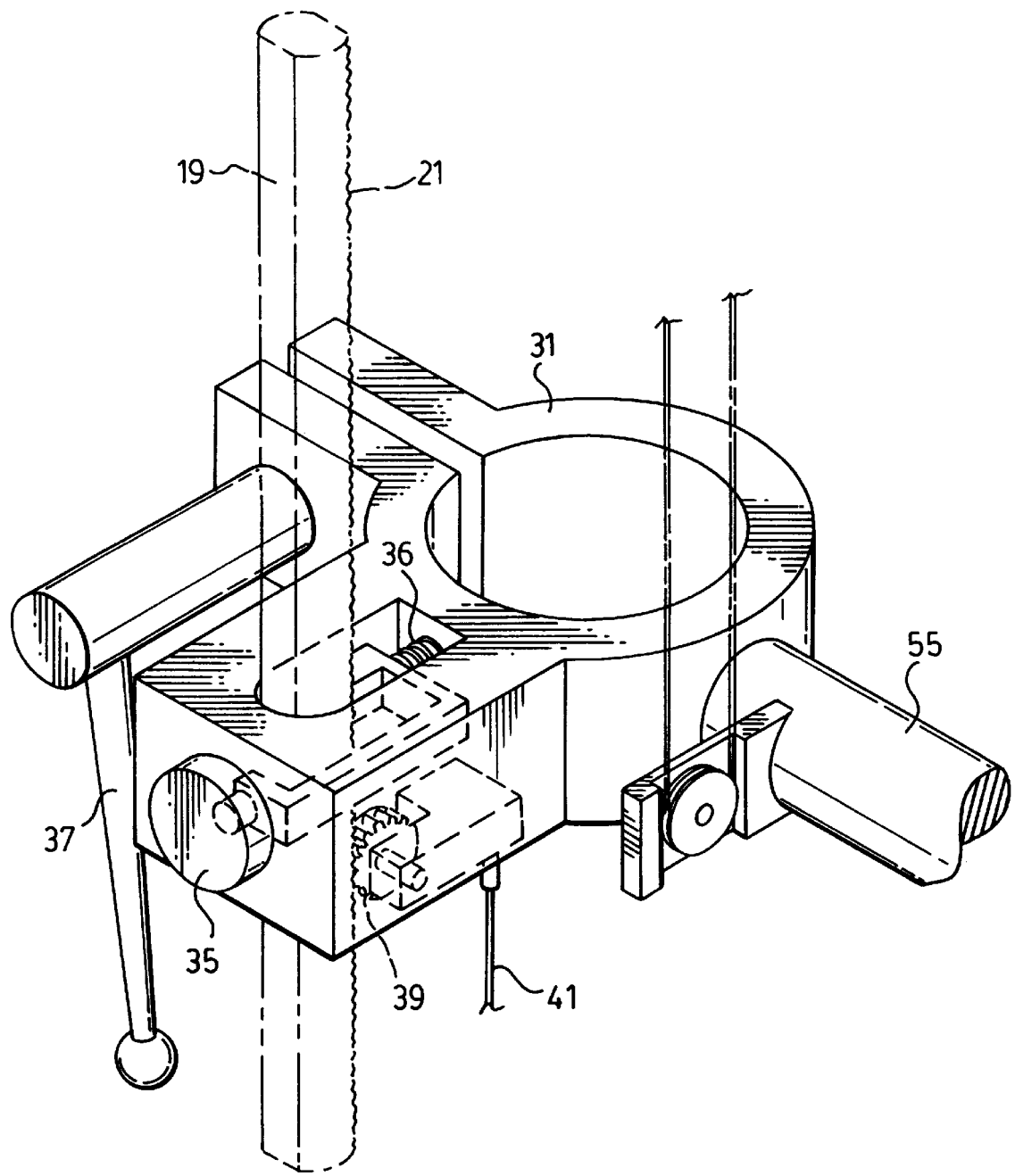
FIG. 3 is an enlarged perspective view of a counter-weighting system used from the testing apparatus of FIG. 2.

Workstation guide 13 includes a main brace 17 as well as a height measuring rod 19 between the lower and upper collars 14 and 15. Measuring rod 19, as best seen in FIG. 3, is provided with a series of teeth 21 which act as height markings on the rod.

Returning to FIG. 2, the lower workstation 29 comprises a main collar 31 which fits over column 9. Provided to one side of the main opening 32 in the collar 31 is a second smaller opening 33. Rod 19 passes through opening 33 as better seen in FIG. 3 of the drawings.

Collar 31 is in the form of a clamp which can be loosened and tightened by means of a lever 37. When the lever is backed off, collar 31 can be rotated around column 9. This also produces rotation of the workstation guide 13 because of the engagement of the measuring rod 19 in collar 31.

The releasing or backing off of lever 37 also facilitates raising and lowering of collar 31 along the column. However in order to perform this function, it is necessary to further release a spring loaded lock 36 which normally engages rod 19. Lock 36 is released by pushing outwardly on the lock button 35 disengaging the lock from the bar as seen in FIG. 3. In this position, collar 31 can be raised and lowered relative to both column 9 and measuring rod 19.

As soon as lock button 35 is released, lock 36 springs back into engagement with the rod preventing the collar 31 from shifting lengthwise along the column. The final locking of the collar is then completed by tightening using the lever 37.

The reason for having the secondary spring lock 36 is to ensure that collar 31 and the workstation that it supports does not move in an uncontrolled fashion as soon as the lever 37 is released. To further prevent this a counterbalancing system which counterbalances weight of the entire workstation is provided to assist in both upward and downward movement of the station along the column and the measuring rod. This counterbalancing system will also be described further in greater detail.

Also provided in the collar is a rotating electronic counter 39 having teeth which engage in and roll along the notches 21 in rod 19 as collar 31 is raised and lowered. This counter automatically and accurately determines height setting of the collar relative to the measuring rod. The height as determined by electronic counter 39 is then fed along output line 41 back to the controller 4.

The upper workstation 87 includes a collar 89 which also fits around column 9. A lever 91 is used for loosening and tightening collar 89. Provided to one side of collar 89 is a small opening 97 through which a measuring rod 25 of the upper workstation guide 19 is fitted. The collar 89 of the upper workstation moves vertically relative to both the column and rod 25 and is provided with a rotating electronic counter the same as that shown in FIG. 3 of the drawings with respect to the collar of the lower work station. Also provided on the upper workstation, which cannot be seen in FIG. 2, is a secondary lock the same as spring lock 36 of the lower work station.

As will be appreciated from the description above, the upper workstation like the lower work station can be both rotated around and shifted vertically of column 9. The exact height of the upper workstation is determined through electronic measurements along rod 25 and the measurements made are fed from the lower end 27 of the rod back to the controller 4.

The rotational positions of the upper and lower workstations, i.e. the angles to which they have been rotated on the column, can be quickly visually determined through the provision of cooperative markings on the guides for the two workstations and on the column itself. More particularly, the upper collar 15 of the lower workstation guide 13 which sits directly below collar 10 on the column is provided with a marking 16. Collar 10 is in turn provided with markings 12 which show the different angles of rotation around the column.

Collar 21 of the upper workstation guide is provided with markings 23 which cooperate with marking 18 on the column collar 18 directly below collar 21.

With the above system of markings, the angle of rotation of either the workstations relative to the base platform is immediately visible.

Each of the workstations is capable of accommodating various different types of workstation tools. These tools are selected according to the particular type of task to be performed at the workstation.

In the embodiment shown in FIG. 2 of the drawings, the lower workstation 29 is fitted with a bar type tool 47 having a stem 49. The workstation itself has a first arm 55 which secures directly to collar 31 and a second arm 71 which is adjustably supported by the first arm 55. The stem 49 of bar 47 fits into the head 73 of arm 71.

Figure 5:
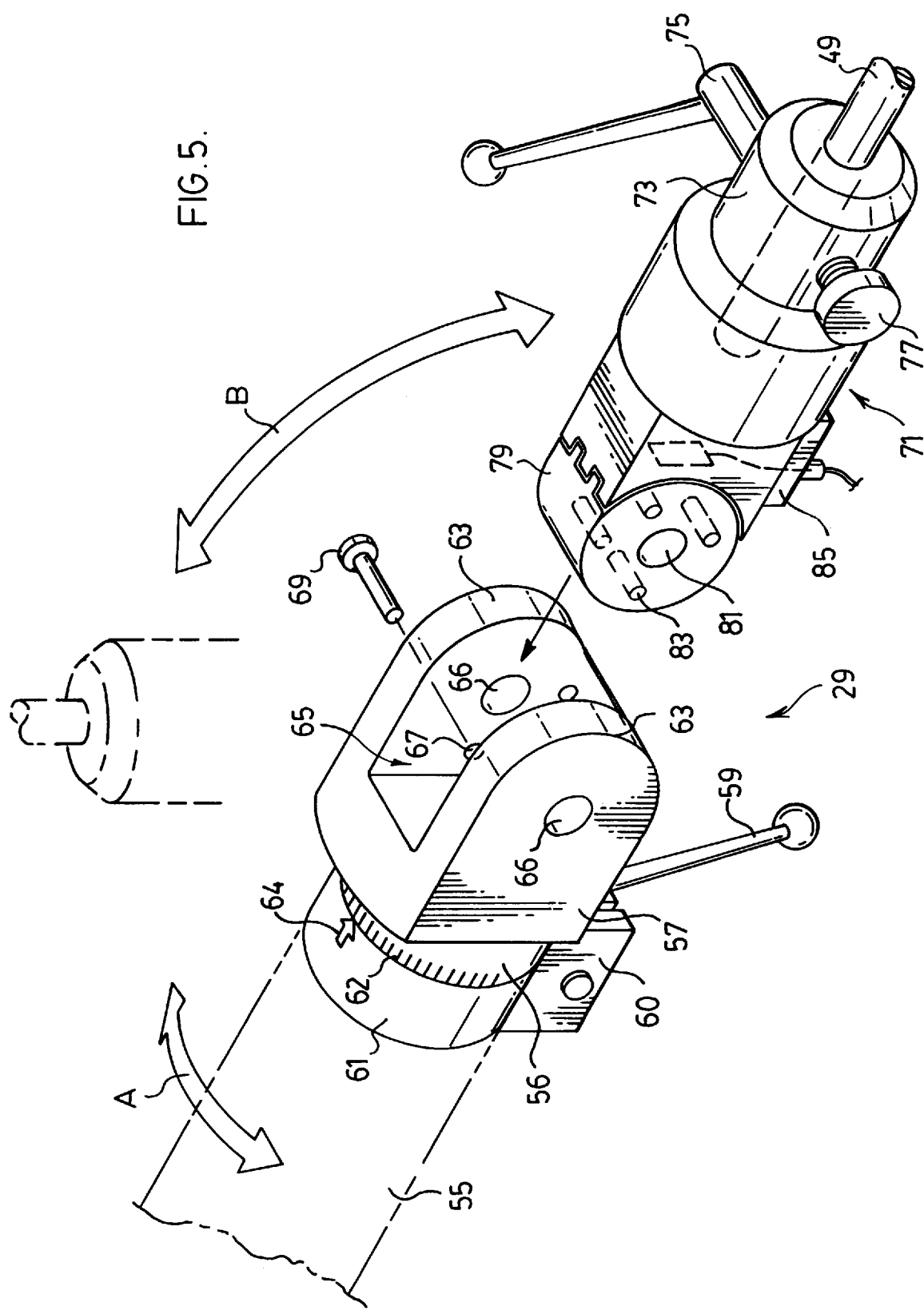
FIG. 5 is an enlarged perspective view showing the adjustment for various different positionings of the workstation from the apparatus of FIG. 2.

FIG. 5 shows in detail the inter-relationship of the two arms 55 and 71 of the lower workstation 29. In particular, receiver 57 for the second or outer arm is provided on the first or inner arm. This receiver is in the form of an adjustable clamp body 60 having a collar portion 61 fitted over arm 55. Arm 55 includes its own collar 56 behind which the collar 61 is trapped. Collar 61 includes a guide 64 which points to rotational positioning markings 62 on collar 56.

Receiver 57 is rotatable on arm 55 as indicated by arrow A in FIG. 5, and can be tightened at any set position by means of clamp lever 59.

The receiver 57 includes a central recess 65 bordered to either side by plates 63. These plates include recesses 66 for receiving a journal pin, which is not shown in the drawings.

Arm 71 has a rounded base 79 which fits into the receiver slot 65. Base 79 includes a center opening 81 which aligns with openings 66 for receiving the journal pin. As will be understood, this provides for an up and down pivoting action of the arm 71 in the direction of arrow B relative to the receiver 57.

The receiver itself is provided with a plurality of pin openings 67 through one of the two side plate 63 as shown. The base 79 of arm 71 is provided with pin receiving openings 83. These openings align with openings 67 in different positions of arm base 79 relative to receiver 57 for receiving a locking pin 69.

FIG. 5 of the drawings shows that arm 71 can be swiveled from an upright to a forwardly extending position and locked in those two positions. Arm 71 can further be locked in different positions between the two shown in FIG. 5 or to different downwardly projecting positions according to which set of openings 67 and 83 are chosen.

FIG. 5 further shows that the stem 49 of tool 47 seats within the head of arm 71. In this particular case, a pair of releasable locking members 75 and 77 are used to provide for the securing and releasing of the tool stem.

As will be understood from the description above, the working tool, e.g. tool 47, can be adjusted by either tipping the tool up and down or by swiveling the receiver for the base of the tool on arm 55. The exact positioning of the tool is chosen according to the particular task to be performed.

When working with a tool such as bar 47, the type of task to be performed is one which would constitute either a pushing or a pulling action on the bar. However, because the bar is fixed in position, it does not move and therefore this is a static as opposed to a dynamic type of test. The actual force on the bar which would indicate the pushing or pulling strength of the individual is determined by means of a load cell 85 provided in the base of arm 71. Cell 85 after measuring the load placed on it passes this information back to controller 4.

FIG. 1 of the drawings shows that the bar style tool of FIG. 1 can be replaced with a table type tool 51. This tool has a base stem 53 identical to the base 49 on tool 47. As will be seen in FIG. 1, table 51 is used with the lower workstation when the second arm 71 is swiveled to an upright position relative to arm 55.

FIGS. 1 and 2 of the drawings show that this same table 51 can also be fitted at the upper workstation. However like the lower workstation, the upper workstation can also be fitted with other types of tools. As earlier noted, the two workstations are preferably set at different rotational positions on the column which allows different tasks to be performed at different working angles while the individual stands on the base platform. This, in combination with the different height settings for the two workstations can be used for assessing different ranges of motion in which the individual is capable of working.

Earlier reference was made to a counterbalancing system for counterbalancing weight of the two workstations. Such a counterbalancing system, which is well shown in FIG. 4 of the drawings, is used to offset the weight of each of the workstations. Therefore, even though the workstations are very heavy they can be moved up and down with nothing more than the touch of a finger once the locks holding them in position have been released. Without the counterbalancing system, movement of the workstations would be extremely awkward and even dangerous.

Figure 4:
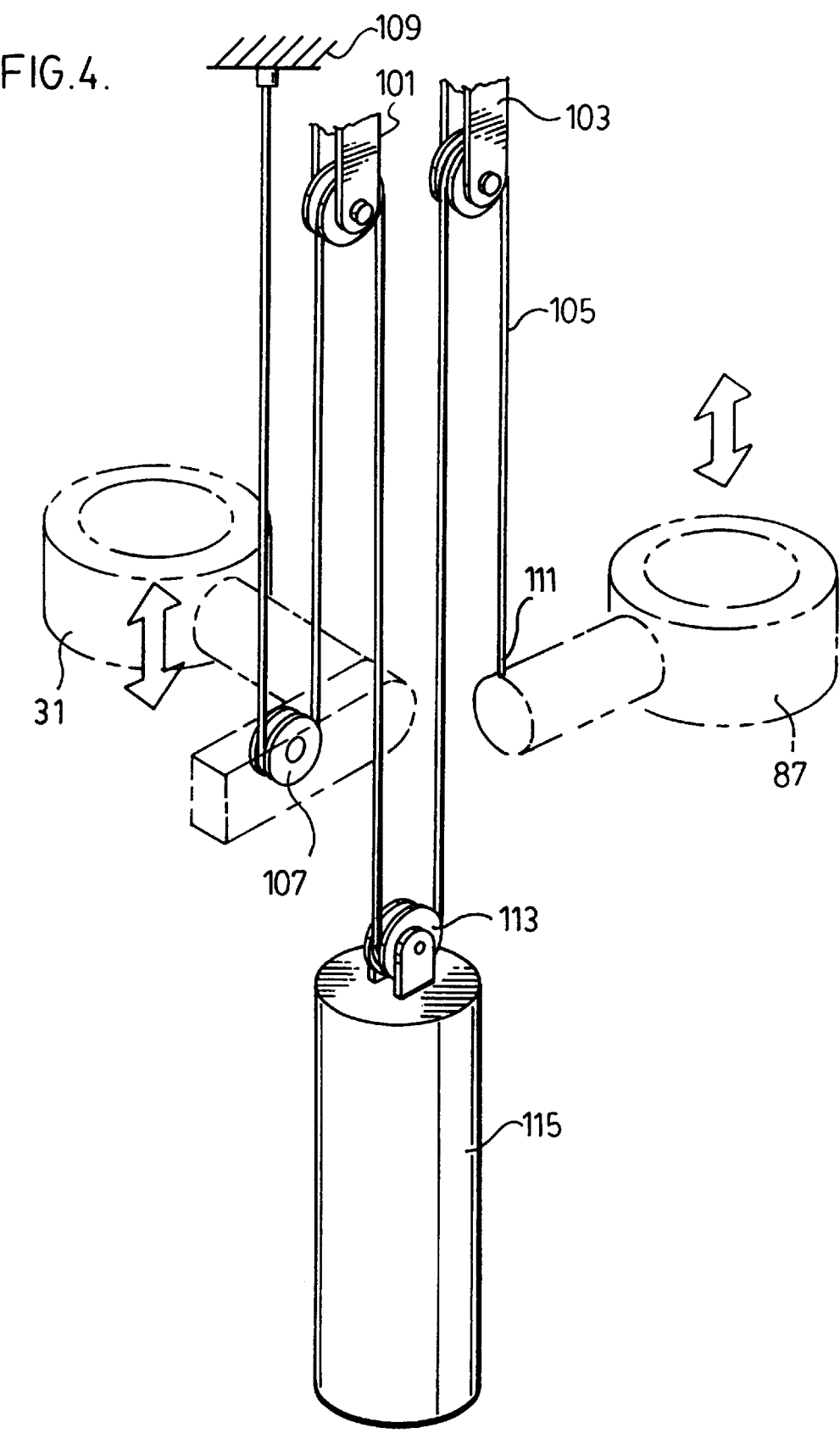
FIG. 4 is an enlarged perspective view of the measuring system for measuring height of the workstation from the apparatus of FIG. 2.

More particularly, the counterbalancing system of FIG. 4 is provided by means of a weight 115 which fits down into the center hollow of column 9. This weight is supported by a single cable 105. Cable 105 passes around a pair of pulleys 101 and 103. Pulley 101 is supported at the upper end of workstation support guide 13 while pulley 103 is supported at the upper end of workstation guide 19. One end of the pulley attaches at 111 to collar 87 of the upper workstation while the other end of the cable passes around a further pulley 107 provided on arm 55 of the lower workstation. The cable then fastens at 109 back to the upper end of the lower workstation guide.

Weight 115 is sufficient to offset the weight of both of the workstations. However, as a result of the arrangement of pulleys both workstations are independently height adjustable using the same counterbalancing assembly. As either or both of the workstations are moved downwardly, the counterbalancing weight is pulled upwardly and if either workstation is moved upwardly, the counterbalancing weight moves downwardly within the column.

Figure 6:
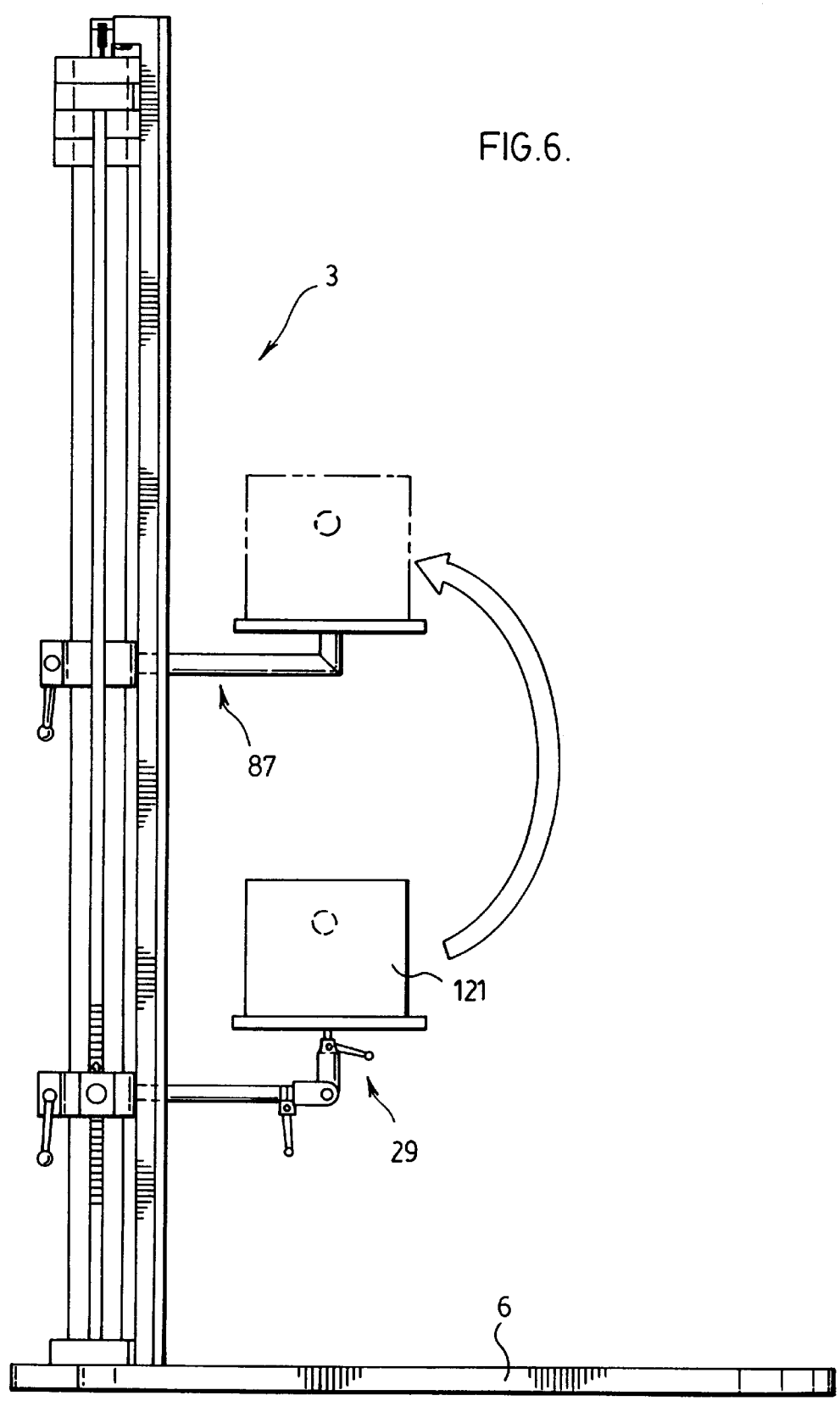
FIG. 6 is a side view of the assembled testing apparatus of FIG. 2.

FIG. 6 shows one task which can be performed using apparatus 3. This task is a dynamic test as opposed to the static test referred to with respect to the use of bar tool 47. As seen in FIG. 6, the apparatus is set up with a pair of table type tools set at different heights and if desired at different angles on the apparatus.

The task shown in FIG. 6 uses a container 21 into which weights are placed. The amount of weight in the container is hidden from an individual who is to perform this particular task. That individual places his or her feet on platform 6 with the exact positioning of the feet being determined by the markings on the platform.

The container starts in a seated position on the lower table. The weight of the container is sensed by the load cell in the lower workstation. The container is then moved by the individual to the upper table. The removing of the load from the lower table is sensed by the load cell in the lower workstation. The placement of the load on the upper table is then sensed by the load cell in the upper workstation. The individual then takes the container from the top table and replaces the container on the lower table. This movement of the container is again sensed by the respective load cells.

The above procedure is repeated a number of different times either with the same weight or with a different weight in the container. Throughout the entire testing procedure, heart rate of the individual is monitored and then fed to the controller. The results of the monitoring are then displayed at the monitor screen 5.

As will be appreciated, the height and angle variation between the upper and lower workstations can be varied to determine range of motion parameters in which the individual is capable of working.

A fraudulent claim for injury can be differentiated from a legitimate claim using apparatus 3. A graphic demonstration of this is provided in comparing the graph results of FIGS. 7 and 8 shown on the monitor screen. In each of these graphs, the X-axis represents strength level while the Y-axis indicates time. In FIG. 7, the graph lines 117, 119 and 121 represent three consecutive lifts with the strength level being the highest and remaining the most constant in the first lift indicated by graph line 117. In the second lift, indicated by graph line 119 the strength level is not as high and falls off more quickly than in the first lift. In the third lift, represented by graph line 121, the strength level is lower still and falls off even more quickly.

The results of the test as represented by FIG. 7 are what would normally be expected of an individual.

FIG. 8 shows three graph lines 123, 125 and 127 representing three consecutive lifts. Graph line 123 is similar to graph line 117 with a relatively high strength level which does not drop off overly quickly. However, graph line 125 representing the second lift shows a lower maximum strength level with that strength level being maintained over a longer period of time. This is a substantially different graph line from graph line 119 in FIG. 7.

Graph line 127 representing the third lift shows a maximum strength level which is higher than the strength levels in both of the two earlier lifts for a very short period of time and which then drops off very dramatically.

The test results shown in FIG. 8 are not typical of what should occur in three successive lifts. FIG. 8 would therefore generally indicate the test results of an individual not consistently operating at his or her peak levels but rather attempting to pretend that a proper effort is being made. As can be seen in FIG. 8, it is generally very difficult to produce proportionately diminishing strength levels over successive lifts and therefore, it is very difficult to "fool" the testing system of the present invention.

As earlier described, FIG. 2 shows that a bar type tool can be fitted to the apparatus and used for sensing pushing and pulling strengths. FIGS. 9 through 13 show a much more sophisticated tool generally indicated at 131 which is again used for testing pushing and pulling strengths. Tool 131 is also used for testing different hand strengths.

Figure 9:
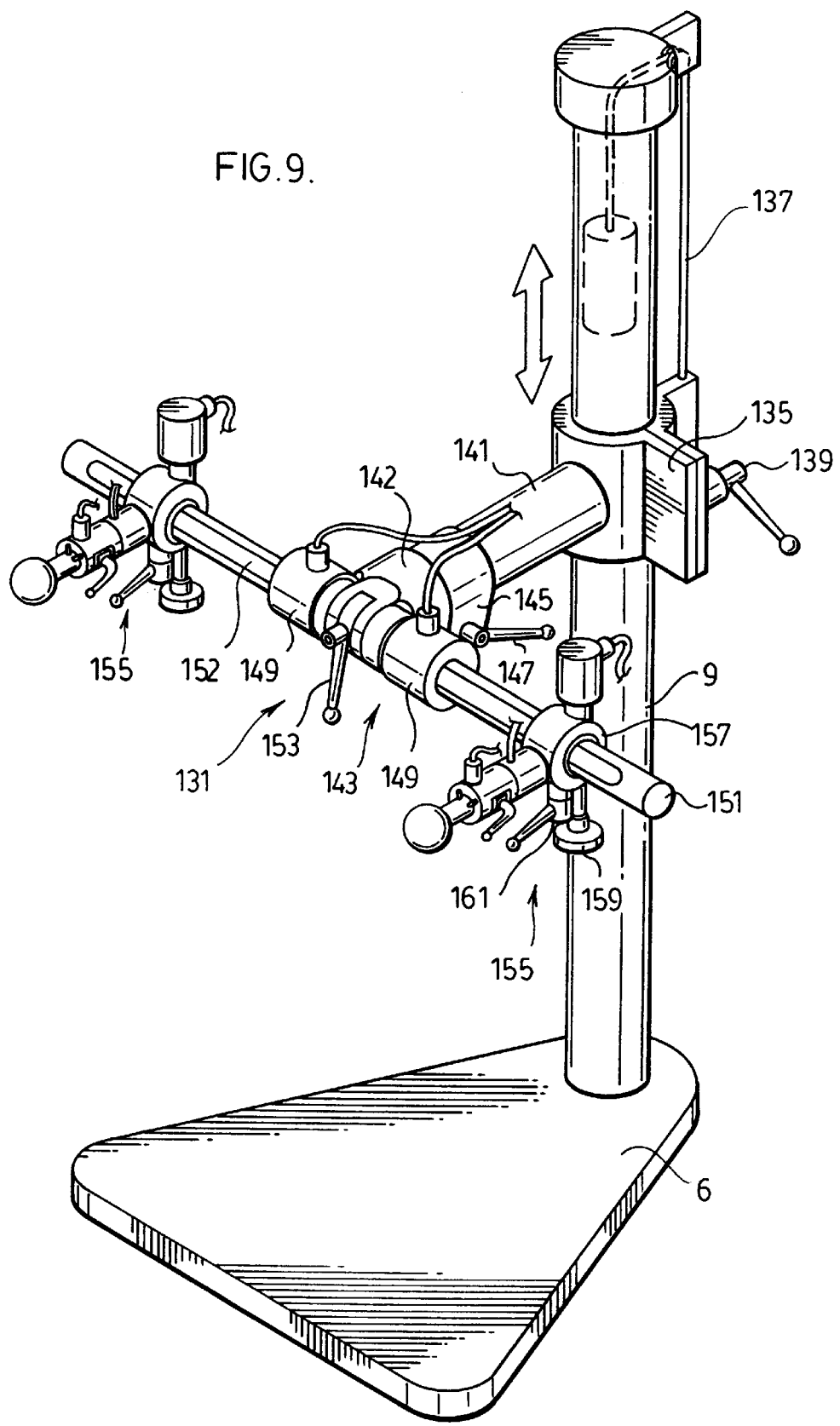
FIG. 9 shows a testing apparatus with a workstation different from that shown in FIG. 1.

Tool 131 has a clamp-like mounting collar 135 which fits onto the column 9 of apparatus 3. As shown in FIG. 9 of the drawings, tool 131 preferably constitutes the entire workstation and replaces both of the earlier described workstations.

A cable 137 extends upwardly from collar 135 around a pulley at the upper end of the column and then downwardly into the column to a counterbalancing weight as shown in FIG. 9. A lever 139 is used to loosen and tighten collar 135 allowing it to move vertically and to rotate around the column. Again, by virtue of the counterbalancing system, tool or workstation 131, although heavy is movable upwardly and downwardly through the touch of a finger.

As will be understood, the height to which the tool is set is determined by the height of the individual who will be using the tool.

A main arm 141 extends from collar 135. This arm is provided at its outer end with a fixed collar portion 142.

A tool support generally indicated at 143 mounts on arm 141. This tool support includes a first collar 145 which is trapped behind a collar 142 on arm 141. Collar 145 is a releasable clamp which is loosened and tightened by means of a lever 147.

The tool mount further comprises an elongated hollow head portion 149 which receives a bar 151. Bar 151 is rotatable to different positions within head portion 149. Once a desired position has been achieved, the bar can be clamped down by adjustable lever clamp 153.

A pair of hand grip assemblies generally indicated at 155 are mounted to the bar on opposite sides of the sleeve-like head portion 149.

Each of the hand grip assemblies 155 includes a mounting collar 157 which fits directly to bar 151. Each of the collars 157 is slideable lengthwise of the bar and can be locked at a specific position by means of a releasable locking member 159. Sensors are provided which sense the exact positioning of each of the hand grip assemblies as well as the separation between the two assemblies. This is important because different gripping tasks should be performed at different spreads of the two assemblies.

The collars 157 of the two hand grip assemblies are also turnable on bar 151 so they can be set at different angles as shown in FIGS. 11 and 12 of the drawings. A lever clamp 161 is provided on each of the assemblies for locking a set angled position for each hand grip assembly.

The ability to change the angle of the hand grip assemblies is also important for different testing procedures. Once again, to ensure accuracy, sensors are provided in the hand grip assemblies which show the exact angles to which the assemblies have been turned on the support bar 151.

It is also to be understood from the description above that both of the hand grip assemblies can be locked either at the same or at different angles on the bar and then the entire bar with the hand grip assemblies locked in position can be rotated. The bar can then be locked in position by lever clamp 153. As shown in FIG. 9, the bar head 149 includes sensors which indicate the degree of rotation of the bar in the head.

FIGS. 10 through 13 show further details of each of the hand grip assemblies. These assemblies include an arm 163 secured to the collar 157. The arm 163 has a center opening 165. Provided at the base of opening 165 is a rotatable male locking part 167. An electronic sensing device 168 measures the rotation of locking part 167, a load sensor 166 is provided beneath the male locking part.

A tool generally indicated at 171 has a stem 173 that fits into the opening 165 on arm 163. The tool stem 173 is provided with a base receptacle 175 that fits over the male locking part 167 within arm 163. The male locking part has a projecting pin which fits into a groove in the receptacle 175 to prevent the tool from rotating relative to the male locking part. Provided on arm 163 is a spring loaded locking pin 170 which locks into a groove 174 on tool stem 173 to rotatably couple the male locking part with the tool stem. The locking pin 170 does not however prevent tool stem 173 from rotating within opening 165.

FIG. 10 of the drawings shows that an individual being tested grips the head 177 of tool 171 for pushing or pulling on or for rotating the tool. Although the tool itself does not move in or out under the pushing and pulling actions the applied forces are measured by the load cell 166 within the support arm for the tool. The range of turning motion of the tool is measured by sensing device 168.

In order to provide proper set up for measuring the turning movement, the receiving arm 163 includes a stop pin 164 while the tool stem includes its own pin 172. These two pins abut one another in the neutral set up position and the tool is rotated to move pin 172 away from pin 163. The tool and its stem are rotatable through a full 360° until pin 172 rotates back against pin 163.

All of the push pull and turning measurements are fed to the controller and displayed on the monitor.

Figure 13:
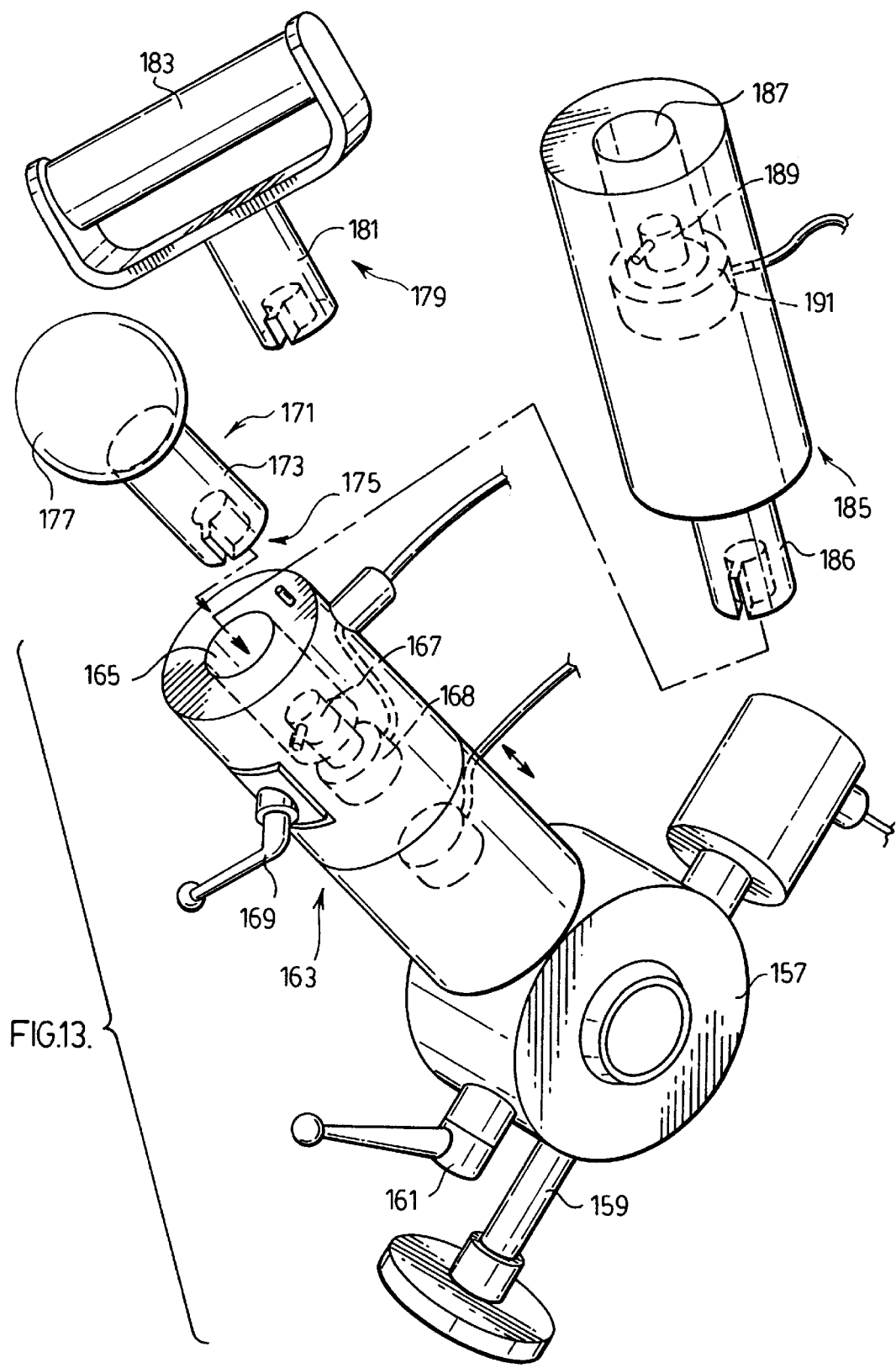
FIG. 13 is an exploded perspective view showing various different set ups for the workstation of FIG. 9.

FIG. 13 of the drawings shows that tool 171 can be replaced with other tools such as tool 179. Tool 179 has a stem 181 identical to the stem 173 on tool 171. However, the head of tool 179, rather than being ball shaped, comprises a handle 183 which allows for different hand positioning. Again, tool 179 can be used for different pushing, pulling and rotational measuring tests.

FIG. 13 shows that a further arm member 185 can be used in conjunction with arm 163 for receiving either one of the tools 171 or 179. Arm member 185 has a stem portion 186 that locks in the opening 165 of arm 163. Arm 185 then has its own opening 187 provided with a male locking member 189 to receive the stems of different tools such as tools 171 and 179. The male locking member 189 is coupled with a load sensor 191.

In this case however, male locking member 189 of arm 185 is fixed in position unlike the rotatable male locking member 167 in arm 163. The stem 186 of arm 185 is secured against rotation within opening 165 of arm 163 by a lever operated clamp 169 and rotational forces applied on the tool fitted within arm 185 are measured by load sensor 191. Therefore rather than giving a range of motion measurement, use of arm 185 provides a rotational strength measurement. It can also be used to provide pushing and pulling strength measurements the same as those earlier described.

Figure 14:
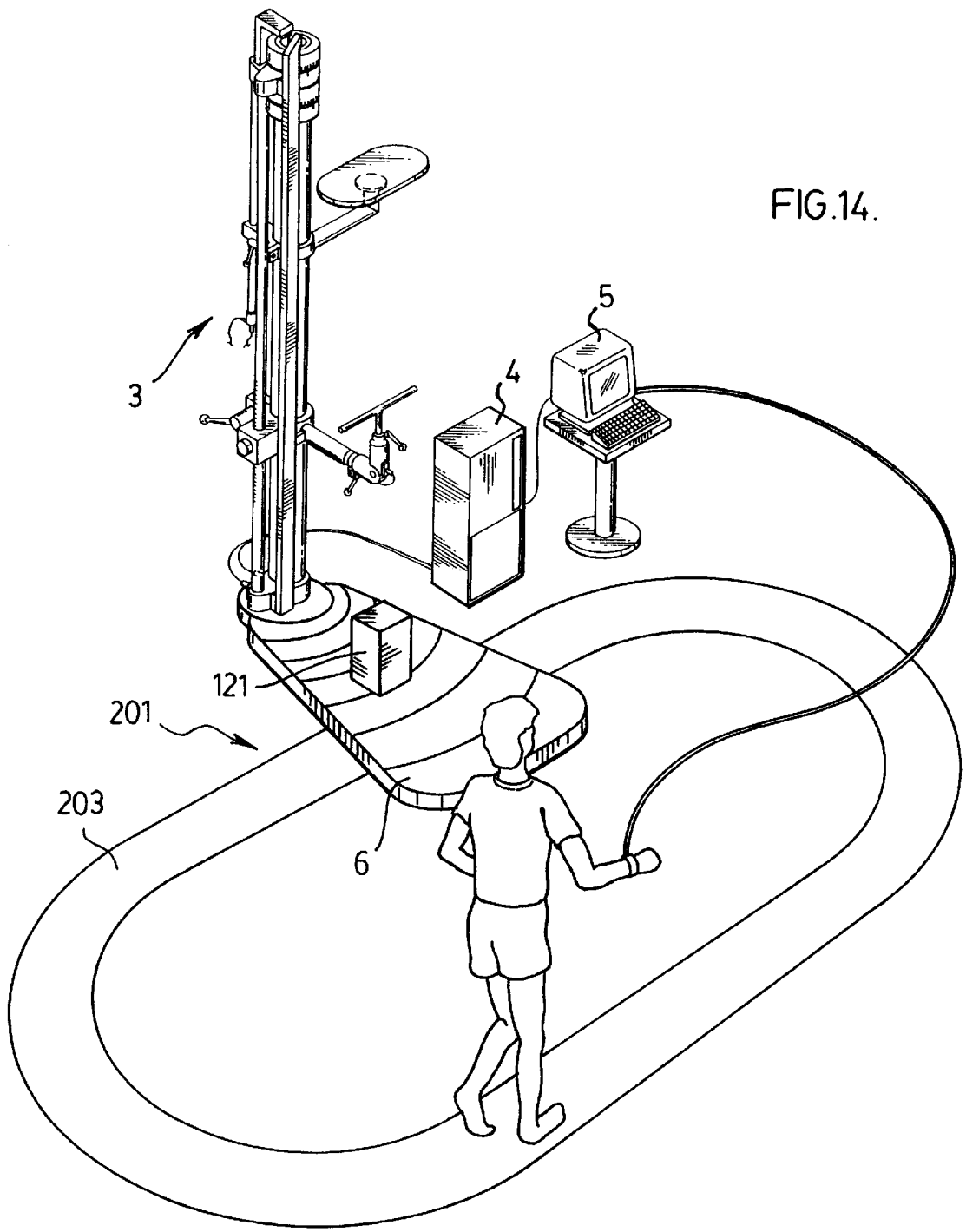
FIG. 14 is a perspective view looking down on a course which is used in a method of assessing an individual's physical capacities.

FIG. 14 of the drawings shows another use of apparatus 3 when used for dynamic testing purposes. In this particular case, apparatus 3 is part of an overall testing circuit generally indicated at 201. This circuit further comprises a circuit course 203 of predetermined distance through which an individual being tested must move. The individual as was the case with the earlier testing procedures is constantly monitored by a pulse sensor 205 which feeds information back to monitor 4.

In this particular set up, the individual lifts the weighted container 121 from the platform 6 of the testing apparatus. A timer is started by the loud sensors in the platform as soon as the weight of the container is lifted off of the platform. The individual carries the container along the length of course 203 and then places the container back on the platform. The load sensors then stop the timer to indicate the length of time that it has taken the individual to complete the course. After a very short rest the individual once again goes through the circuit carrying the container. The container may be loaded with either the same or a different weight. The individual continues this procedure until reaching a specified fatigue level which is assessed by the pulse monitor. The amount of work required to reach this fatigue level is easily determined by the monitoring the time taken to complete the different circuits and the amount of weight moved by the individual. This then shows the physical capacity of the individual.

It will be seen from the above that a whole host of different test procedures can be performed under safely monitored conditions using the testing system of the present invention.

Although various preferred embodiments of the present invention have been described in detail, it will be appreciated by those skilled in the art, that variations may be made without departing from the spirit of the invention or the scope of the appended claims.

The embodiments of the invention in which an exclusive property or privilege is claimed are defined as follows:

1. A physical capacity assessment system including a testing apparatus at which physical tasks are performed, said apparatus having a support base, a column extending upwardly from said base, a first workstation to which load is applied when the tasks are performed, said workstation being supported by and being adjustable in a number of different planes relative to said column, position indicating means which shows positioning of said workstation, said position indicating means including electronic sensors which accurately determine vertical positioning of said workstation on said column and means which measures load placed on said workstation.

2. A system as claimed in claim 1, including an arm extending from said collar, said arm having first and second arm portions, said first arm portion being supported by said collar, said second arm portion being pivotally supported by said first arm portion remotely of said collar.

3. A system as claimed in claim 2, wherein said workstation includes a load receiving member which is selected from a group of members all of which are interchangeably fittable with said second arm portion of said arm of said workstation.

4. A system as claimed in claim 3, including a load cell in said second arm portion, said load cell providing an electronic sensing of any load placed on said load receiving member.

5. A system as claimed in claim 3, including a second workstation having a construction the same as that of said first workstation, said first and second workstations being at different heights on said column and adjustable independently of one another.

6. A system as claimed in claim 5, including a counterbalancing system common to both of said first and second workstations for counterbalancing weight thereof, said counterbalancing system comprising a single cable passing around a series of pulleys on said first and second workstations and a weight on said cable, said weight being located within and movable vertically of said column.

7. A system as claimed in claim 3, wherein said load receiving member comprises a flat table and wherein said system includes a weight receiving container which removably seats atop said table.

8. A system as claimed in claim 1, wherein said workstation includes an elongated bar having spaced apart hand tools thereon and, wherein said bar is rotatably held within a first collar which is provided on a first end of a post of said workstation, said post having a second end which is secured by a second collar to said column.

9. A system as claimed in claim 8, wherein said second collar includes an adjustable clamp for loosening and tightening of said second collar to adjust height setting and rotational positioning of said workstation on said column and said first collar includes an adjustable clamp for rotating and tightening said bar in said first collar.

* * * * *